United States Patent [19]

O'Connor

[11] Patent Number: 5,460,976

[45] Date of Patent: Oct. 24, 1995

[54] DETECTION OF REPRODUCTIVE HORMONE LEVELS IN EQUINES

[75] Inventor: Michael O'Connor, Dublin, Ireland

[73] Assignee: Enfer Technology Limited, Dublin, Ireland

[21] Appl. No.: 748,762

[22] Filed: Aug. 23, 1991

[30] Foreign Application Priority Data

Aug. 23, 1990 [IE] Ireland ..................................... 658/90
Sep. 9, 1990 [IE] Ireland ..................................... 852/90

[51] Int. Cl.⁶ .......................... G01N 33/74; G01N 33/53; A61D 19/00
[52] U.S. Cl. .......................... 436/510; 436/518; 436/806; 436/817; 514/12
[58] Field of Search ..................................... 436/510, 518, 436/817; 514/12; 435/806

[56] References Cited

U.S. PATENT DOCUMENTS 4,952,569  8/1990  Simons ..................................... 424/88

FOREIGN PATENT DOCUMENTS 2118300  10/1983  United Kingdom .

OTHER PUBLICATIONS

Koskinen et al. "Predicting ovalation in the mare on the basis of follicular growth and serum oestrone sulphate and progesterone levels," Zeutrabl Veterinamed 36:299-304 (1989) Abst.

Evans et al; J. Reprod. Fert. Suppl. 23(1975) pp. 193–200.
Peters et al; Abstract #5948 Vet. Bull. Aug. 90, 60(8).
Campbell, Program for Appl. Res. on Fert. Reg. Aug. 1985, 3(5).
Serum Concentrations of FSH,LH and Progesterone During The Oestrous Cycle and Early Pregnancy in the Mare.
Evans, M. J. & Irvine, C. H. G., J. Reprod. Fert. Suppl. 23(1975), 193–200 Investigations on Mare Plasma Using the Progesterone EIA–SSW Technique.
Peters, et al, Abstract #5948, Vetinary Bulletin, Aug. 90, 69(8) Methods of Monitoring Ovarian Function and Predicting Ovulation.
Campbell, K. L. Program for Appl. Res. on Fert. Reg. Aug. 85, 3(5).
P. Rathnam et al., "Isolation and Amino Acid Sequence of the α–Subunit of Follicle–Stimulating Hormone from Equine Pituitary Glands," J. Biol. Chem., vol. 253, No. 15, pp. 5355–5362, Aug. 19, 1978.
Y. Fujiki et al., "Amino Acid Sequence of the β–Subunit of the Follicle–Stimulating Hormone from Equine Pituitary Glands," J. Biol. Chem., vol. 253, No. 15, pp. 5363–5368, Aug. 10, 1978.

*Primary Examiner*—Michael P. Woodward
*Attorney, Agent, or Firm*—Jacobson, Price, Holman & Stern

[57] ABSTRACT

A method of predicting ovulation and a test kit is described which allows one to accurately predict the time of ovulation in an animal in advance thus permitting the highest rate of pregnancy to be achieved and at the same time minimising embryonic death. Also described is a test kit for detecting and quantifying a given reproductive hormone and a method of optimising fertility in animals.

6 Claims, No Drawings

DETECTION OF REPRODUCTIVE HORMONE LEVELS IN EQUINES

The present invention relates to fertility problems in animals, particularly in horses, cows, sheep and pigs, and provides methods by which animal fertility can be maximised.

The fertility rate in thoroughbred horses is approximately 60%. This poor level of fertility is caused by a number of factors including the mating of mares too early in the breeding season when hormone levels may not be optimal; limiting the use of the stallion so that the mare is not covered at the time of ovulation; hormone imbalances in a mare as a result of a strenuous racing career and the mating of stallions and mares which are not selected for fertility but rather for their racing performance.

To obtain high conception rates, low reproductive wastage and high foaling rates in the mare, it is necessary to cover the mare with a highly fertile fresh stallion 12–24 hours prior to ovulation. This timing is critical to allow sperm to set up adequate reservoirs in the reproductive tract of the mare, and for final maturation or capacitation of sperm to take place in the uterus/oviducts before ovulation. Although stallion spermatozoa can survive for 3–5 days in the reproductive tract of the mare, they have highest fertilizing capacity within 24 hours of covering. In contrast, the fertile life span of the ovulated ovum is estimated to be of short duration ie. 8–12 hours, and hence, the critical necessity of cover the mare at the optimum time before ovulation.

However, because the duration of oestrus is variable, but generally of 4–7 days duration in the mare, and ovulation generally occurs 24–48 prior to the end of oestrus, it is difficult to predict accurately during oestrus when the mare will ovulate, and hence when to cover her. Following the regression of the corpus luteum and resulting decline in progesterone in the non-pregnant mare, the follicle continues to grow and oestradiol levels increase. The mare comes in season and the follicle increases in size by 2–3 mm per day and oestradiol levels rise concommitantly with the increased size of the follicle. The follicle reaches a plateau in size and oestradiol levels begin to decline 1–2 days before ovulation. As the follicle grows it probably produces increasing levels of a peptide hormone called inhibin; this hormone suppresses FSH in blood, thereby allowing only the single, but sometimes two, ovulatory follicles to mature. Thus inhibin plays a key role in suppressing FSH during oestrus to maintain the ovulation rate of mares at 1 in the majority of cases. As the ovulatory follicle develops during early oestrus, the increasing oestradiol is responsible for dilation of the cervix, decreased uterine tone and exhibition of more intense signs of oestrus prior to ovulation.

In a recent study by Woods et al (Ref. 4) it has been shown that the optimum time for insemination of mares is about one day prior to ovulation. The study showed that if insemination took place one day before ovulation 89% of inseminated mares became pregnant and of those pregnancies 14% later exhibited embryonic death. When insemination took place on the day of ovulation there was a 52% pregnancy rate with a 34% embryonic death rate. Insemination the day after ovulation resulted in a 6% pregnancy rate and a 33% embryonic death rate.

Even the most comprehensive rectal examination of mares which is currently undertaken in which the ovaries are monitored with an ultrasonic scanner, via the rectum, every three hours will only show ovulation when it occurs. The above described study shows that insemination on that day will only result in a 52% pregnancy rate with a subsequent 34% embryonic death rate.

It is known that oestradiol, or a major metabolite oestrone S04, increase daily during oestrus, plateau and decline before ovulation.

Thus, this pattern of oestradiol could be used to time or predict ovulation accurately. However, this observation was of no major practical benefit to the stud manager because of the lack of a reliable, fast (results the same day) assay for oestradiol.

It is thus an object of the present invention to be able to accurately predict the time of ovulation in advance allowing the highest rate of pregnancy to be achieved and at the same time minimising embryonic death. A further object is to provide a fast, reliable assay to determine ovulation, particularly one which accurately measures small amounts of reproductive hormones.

A number of different techniques are currently used to optimise pregnancy. The mares are checked by swabbing for uterine and cervical infections and are then treated with antibiotics if they are found to be infected. The ovary can be manually manipulated by the veterinary surgeon to detect a large follicle thus determining that the mare is approaching ovulation. Ultrasonic scanning techniques are used to detect pregnancy early on. Empirical treatments are also used in which combinations of hormones are administered to mares which gives wide variations in results and usually no pregnancy is achieved. Finally, a combination of progesterone therapy and a lighting regime are used in order to fool the mare into thinking that it is spring. The mares are subjected to eight weeks of increased exposure to electric light, the nutritional level is elevated and their heating is increased. This causes a small flow of hormones in the mare and Follicle Stimulating Hormone (FSH) and Lutinizing Hormone (LH) to be produced by the anterior pituitary gland. Then 500 mg of progesterone is given by injection. The progesterone stops the activity of the anterior pituitary gland and when the progesterone level falls off again a larger amount of FSH and LH are believed to be released. The mare then progresses into an estrus cycle and comes in heat. This latter technique has a reasonable success rate compared with no intervention at all and 50% of mares subjected to this treatment may respond.

The particular level of any hormone in the blood stream at any given time taken together with the levels of any of the other hormones involved in pregnancy will cause a specific physiological effect on the reproductive process. It is therefore important to be able to access the level of a hormone in order to optimise pregnancy. If a given hormone is not increasing in concentration in the bloodstream as quickly as it should, it would be possible to immediately administer an appropriate amount of the hormone to optimise the estrus cycle.

In a normally cycling mare three to seven Graafian follicles will develop in the ovary, under the influence of small levels of FSH and LH, to a size of greater than 18 mm. This can be determined by ultra-sonic scanning. From day seven to day ten of the cycle selection of one or possibly two of these follicles takes place so that the follicle matures and increases in size. The trigger for maturation of the follicle appears to be a surge in the concentration of FSH in the bloodstream which takes place at about day seven of the cycle. It is believed that among the follicles developing at any one time, one follicle has a better capillary network which allows for an increased exposure to FSH in that particular follicle. As this faster developing follicle grows it switches off the other follicles causing them to degenerate, probably by the presence of a local hormone. Thus an appropriate level of FSH must be maintained between day seven and day ten in order to ensure release of an ovum.

Oestradiol is a hormone which peaks 48 hours before ovulation, so an ability to determine oestradiol levels would allow for mating to be timed to the point of peak fertility. High levels of the hormone prolactin in both stallions and mares leads to a high level of infertility, which can be treated with bromocryptine. Thus by accurately determining prolactin levels fertility can be enhanced. Leutinizing hormone (LH) levels rise at approximately day fourteen of the cycle causing the Graafian follicle to rupture and leading to ovulation. Determination of LH levels permits mating to take place at the time when conception is most likely to occur.

It is thus a further object of the invention to provide a method to determine the actual level of any of the reproductive hormones in an animal thus allowing any imbalance in hormone levels to be corrected and also allowing mating to take place at a time which is most likely to lead to pregnancy.

It has surprisingly been found that human antibodies directed against the above described reproductive hormones are also capable of reacting with animal hormones, particularly equine hormones.

For example, FSH occurs in mammals as a two sub-unit glycoprotein, the two sub-units being non-covalently bound and referred to as the alpha and beta sub-units. Biological activity resides in the beta sub-unit. Although similar to an extent, FSH from different species varies in its molecular size, amino-acid sequences and conformational folding (references 1, 2 and 3).

Comparing FSH from horses with that from humans shows:

1) the alpha sub-unit to be 10 amino acids shorter in equine FSH, 2) the alpha sub-unit to differ at 26 amino acid positions between equine and human FSH and 3) the beta sub-unit contains 6 amino acid differences almost equally spaced along its 118 residues.

The equine molecule is therefore different from the human molecule.

It is particularly surprising to find cross-reactivity between the two types of FSH using a monoclonal antibody since monoclonal antibodies are generally regarded to be specific and normally monoclonal antibodies are designed to avoid cross-reaction or decreased specificity. For a monoclonal antibody to be specific for FSH it must be an antibody raised against the beta sub-unit or it must recognise part of the beta sub-unit together with part of the alpha sub-unit, since identical alpha sub-units are found in FSH, Thyroid Stimulating Hormone (TSH), LH, and Chorionic Gonadotrophin (CG) within a single species.

Anti-human FSH monoclonal antibodies are available from a number of commercial sources including Amersham International, Plc., England, York Biologicals International, New York, U.S.A., and Immuno Search, New Jersey, U.S.A. Anti-human prolactin monoclonal antibodies, anti-human oestradiol polyclonal antibodies and anti-human progesterone polyclonal antibodies are also commerically available from a number of sources including Amersham International Plc.

According to the present invention there is provided a method of predicting ovulation in an animal comprising determining the level of a reproductive hormone in the bloodstream using an anti-reproductive hormone antibody. Ovulation may be predicted from a peak in oestradiol levels or from the lowest level of FSH. Preferably the antibody is an anti-human antibody.

According to a further aspect of the present invention there is provided a method of detecting and quantifying a given reproductive hormone in animals in which an anti-human antibody directed against the given hormone is utilized in an immunometric assay.

In a further aspect the invention relates to an anti-human anti-reproductive-hormone antibody for use in the determination of reproductive hormone levels in animals.

In a further aspect the invention provides a test kit for the detection of reproductive hormones in animals by immunometric assay utilizing an antibody as described above. In a particular embodiment the test kit comprising anti-oestradiol or anti-FSH antibodies may be used to predict ovulation. Many such assays are available such as chemiluminescence assays, enhanced luminescence assays, radioimmunoassays and enzyme linked assays, all of which fall within the scope of this invention.

The anti-human antibody may be a monoclonal antibody. The reproductive hormones detectable by this system include FSH, progesterone, prolactin, and oestradiol. The animals may be horses, sheep, cattle or pigs.

The Amerlite (TM) system marketed by Amersham International Plc, England is a non-radioactive immunoassay system for the detection of hormone levels in humans. The present invention also relates to a non-radioactive immunoassay system of the same type as the Amerlite system for use in the detection of reproductive hormone levels in animals, particularly equines.

In a particular embodiment the invention relates to a test kit for the detection of FSH in equines by immunometric assay comprising an anti-human anti-FSH monoclonal antibody. Preferaby the monoclonal antibody is a mouse anti-human antibody.

The invention further relates to a method of optimising fertility in animals comprising:

(i) determining the level of at least one reproductive hormone in the animal by means of an immunometric assay which utilizes an anti-human, anti-reproductive hormone antibody, and (ii) adjusting the level of the hormone to a nomal level either by administering hormone to the animal or by administering a drug to lower the hormone level.

The invention also provides a method of maximising pregnancy in animals comprising:

(i) determining the level of a reproductive hormone, selected from FSH and oestradiol, in the bloodstream of the animal by means of an immunometric assay which utilizes an anti-human, anti-reproductive hormone antibody, and (ii) inseminating the animal within 48 hours of the occurance of either the peak level of oestradiol, or the lowest level of FSH, or both.

Using the techniques of the present invention fertility and pregnancy can be maximised in a number of ways:

(1) Determine if Mare is Anoestrus: the anovulatory anoestuous mare can be accurately diagnosed by measurement of progesterone in the blood of mares taken at 4–7 day intervals. Low progesterone in a sequence of 4 samples taken at 4–7 day intervals is conclusive evidence that the mare is anoestrus. Presence of elevated progestrerone (greater than 1 ng/ml) in one or more samples is evidence of the presence of a corpus luteum and hence that the mare has ovulated. This information is particularly valuable during the transition from the non-breeding to the breeding season.

(2) Confirmation of Ovulation: following covering in oestrus, one or more blood samples can be taken, progesterone levels determined and a value of greater than 1 ng/ml is confirmation that the mare have ovulated.

(3) Prolonged Dioestrus: a non-pregnant mare that fails to show oestrus 21–24 days after a previous oestrus (ie. foal heat) can be suspected to have prolonged maintenance of the life span of the corpus luteum (in non-pregnant mares it should repress after 14–16 days due to endogenous release of prostaglandin F2 alpha in the absence of the embryo). This can be confirmed by taking a blood sample after the failure to come in season 21–24 days after the previous oestrus and measuring progesterone in it. High levels of progesterone (greater than 1 ng/ml) confirm that the mare is still in oestrus and appropriate veterinary treatment is required.

(4) Primary Luteal Insufficiency: following covering, ovulation and conception in the mare, a small percentage of mares may secrete inadequate levels of progesterone to maintain viability of the embryo (require levels greater than 2ng/ml). Such mares could be identified by taking and measuring progesterone concentrations in 2–3 daily blood samples taken 6 or 7 days after ovulation.

(5) Check function of Accessory Corpora: in the pregnant mare the endometrial cups are formed at 38–40 days of pregnancy and they produce equine chorionic gonadotrophin (eCG or formerly called PMSG) which is responsible for the formation of accessary corpora lutea. These then produce large quantities of progesterone essential for continued maintenance of pregnancy and viability of the embryo. If either insufficient eCG is produced or the accessory corpora lutea are inadequate, the continuance of pregnancy might be jeopordized. Measurement of progesterone in 2–3 samples taken after day 60 could help to confirm or not, that progesterone levels were adequate. This use, although not of general overall significance, could be important in those mares prone to lose a pregnancy between days 45 and 150.

The invention will now be described in greater detail in the following Examples. The FSH assay was carried out with the Amerlite System which is a complete immunoassay system comprising:

i) An analyser, which is an integrated luminescence reader with a data reduction system, and microprocessor, (ii) A microtitre plate washer, (iii) An incubator/shaker, (iv) A pipetting station—either manual or robotic, (v) An interface to an IBM-compatible personal computer—with "RIA calc" data reduction facilities, (vi) An appropriate immunometric assay kit.

In each case hormone levels in serum samples from six horses were assayed.

EXAMPLE 1

FSH assay

A commercially available kit for the detection of human FSH was utilised in this example (available from Amersham International Plc.). The wells of the microtitre tray in the kit are coated with sheep anti-FSH monoclonal antibody. The standard/control/sample was added to the wells. A mouse monoclonal anti-human anti-FSH antibody which is linked to horseradish peroxidase was then added and allowed to equilibrate for one hour at 37° C. The unbound conjugate of monoclonal antibody and peroxidase was removed by aspiration and washing. A "signal" reagent (containing luminogenic substrates and a peracid salt) with enhancer was then added into the wells. A complex reaction between peroxide, luminol and peroxides takes place in which the peroxidase oxidises the luminogenic substrate and this oxidation reaction causes the emission of light.

The enhancer is a substituted phenol which increases the level of light produced and prolongs its emission. Because the light levels from enhanced luminescence are of high intensity, the reaction can be optimized to give a continuous output of light rather than a flash. The light signal can be measured without critical timing and the signal can be re-measured if desired.

The evolved light is measured at 2 to 20 minutes post-addition of signal and enhancer. The amount of conjugate bound to the wells is directly proportional to the concentration of FSH present in the standard/control/sample. The results of this test are shown in Table 1.

It is also possible to determine FSH levels in a sample using a non-competitive "sandwich-type" immunometric assay system.

EXAMPLE 2

Oestradiol assay

Oestradiol levels were determined by a competitive radio-immunoassay which uses donkey anti-rabbit antibody and rabbit anti-human anti-oestradiol polyclonal antibody. Radioactively labelled oestradiol and cold standard/controls/sample are then added into the assay system where they compete for binding sites on the bound anti-oestradiol antibody. The amount of radioactive label bound is inversely proportional to the amount of oestradiol in the sample. The oestradiol assay utilises a rabbit anti-oestradiol polyclonal antiserum which allows for some cross-reactivity with oestradiol-3-sulphate, oestrone and oestriol.

The results are shown in Table 1.

EXAMPLE 3

Progesterone and prolactin levels were also determined using polyclonal and monoclonal anti-human antibodies respectively. The results are shown in Table 1.

TABLE 1

| Amerlite controls:- | | "Tru-value" controls | |
|---|---|---|---|
| FSH mIU/ml (MONOCLONAL) | | | |
| Low = | 10.3 | Low = | 5.7 |
| Medium = | 25.0 | Medium = | 28.3 |
| High = | 50.2 | High = | 70.2 |
| Patient I = | 1.6 | — | Pregnant Mare |
| Patient II = | 3.8 | | " |
| Patient III = | 14.5 | — | Cycling Mare |
| Patient IV = | 14.0 | | " |
| Patient V = | 13.5 | | " |
| Patient VI = | 36.9 | — | Gelding |
| PROLACTIN mIU/L (MONOCLONAL) | | | |
| Low = | 269 | Low = | 12.2 |
| Medium = | 1334 | Medium = | 1817 |
| High = | 5678 | High = | 5080 |
| Patient I = | 21.6 | — | Pregnant Mare |
| Patient II = | 208 | | Pregnant Mare (milk "comming-in") |
| Patient III = | 29.0 | — | Cycling Mare |
| Patient IV = | 28.9 | — | " |
| Patient V = | 48.7* | (117.7) | " |
| Patient VI = | 32.0 | — | Gelding |

*Results of serum samples differed from mean results of plasma samples.

| OESTRADIOL pmol/L (POLYCLONAL) | |
|---|---|
| RSL Controls | Wein Controls |

TABLE 1-continued

| | | | | |
|---|---|---|---|---|
| Low = | 286 | | Low = | 293 |
| Medium = | 619 | | Medium = | 2621 |
| High = | 1841 | | High = | 5182 |
| Patient I = | 10938* | — | Pregnant Mare | |
| Patient II = | 11889* | — | " | |
| Patient III = | 240** | — | Cycling Mare | |
| Patient IV = | 520** | — | " | |
| Patient V = | 240** | — | Cycling Mare | |
| Patient VI = | 325 | — | Gelding | |

*Cross-reaction with oestriol?
**Levels compatible with mares in oestrous phase of cycle and correlates with FSH results.

PROGESTERONE nmol/L (POLYCLONAL)

| Amerlite Controls | | RSL Controls | | Wein Controls | |
|---|---|---|---|---|---|
| Low = | 0.31 | Low = | 0.92 | Low = | 2.4 |
| Medium = | 10.9 | Medium = | 27.0 | Medium = | 21.4 |
| High = | 56 | High = | 72.8 | High = | 51.3 |
| Patient I = | 6.0 | — | | Pregnant Mare | |
| Patient II = | 7.0 | — | | " | |
| Patient III = | N.D | — | | Cycling Mare | |
| Patient IV = | N.D | — | | " | |
| Patient V = | N.D | — | | " | |
| Patient VI = | N.D | — | | Gelding | |

N.D. = Not Detected.

EXAMPLE 4

A trial was conducted on a total of 112 mares in which oestradiol and FSH levels in peripheral blood were determined daily over the period in which the mare was in heat, by the techniques discussed in Examples 1 and 2. The mares were also examined by a clinician using conventional techniques for determining ovulation e.g. rectal examination for development of the size softness and contour of the follicles, and relaxation of the cervix. Ultrasonic scanning was also used to measure follicle growth and to determine when ovulation had occured based on the disappearance of the pre-ovulatory follicle and the presence of a corpus haemoragium in its place the next day.

A comparison of peak hormone levels with time of ovulation showed that 84.6% of mares ovulated within 48 hours of the oestradiol peak. In 60% of mares the FSH level fell to its lowest point at the same time as the oestradiol level peaked.

The assay proved to be rapid and accurate and has the advantage that it does not involve the use of radioisotopes or other hazardous chemicals.

REFERENCES

Fujiki Y., Rathnam P. and Saxena B. B., Amino acid sequence of the subunit of the Follicle Stimulating Hormone from equine pituitary glands, J.Biol Chem. 253.5363–5368, 1978.

Hojo H. and Ryan R. J., Monoclonal antibodies against human Follicle Stimulating Hormone, Endochrinology, 2428–2434, 1985.

Rathnam P., Fuijiki Y., Landefeld T. D. and Saxena B. B., Isolation and amino acid sequence of the alpha subunit of Follicle Stimulating Hormone from equine pituitary glands, J. Biol. Chem. 253.5355–5362, 1978.

Woods J., Bergfelt D. R. and Ginter O. J., Effects of time of insemination relative to ovulation on pregnancy rate and embryonic loss rate in mares. Equine Veterinary Journal. 22 (6) 410–415, 1990.

I claim:

1. A method of predicting ovulation in an equine comprising determining the level of follicle stimulating hormone or oestradiol in a blood sample from the equine by enhanced luminescence immunometric assay using an antibody against human follicle stimulating hormone and an antibody against human oestradiol, wherein detection of both a maximum level of oestradiol and a minimum level of follicle stimulating hormone indicates ovulation will occur within 48 hours.

2. The method of claim 1 comprising incubating the blood sample from the equine with the antibody against human follicle stimulating hormone and the antibody against human oestradiol in the enhanced luminescence immunometric assay, and detecting the amount of antibody/follicle stimulating hormone complex and antibody/oestradiol complex.

3. The method of claim 2, wherein the antibody against human follicle stimulating hormone and the antibody against human oestradiol are monoclonal antibodies.

4. The method of claim 3, wherein the monoclonal antibodies are mouse antibodies.

5. The method of claim 2, wherein the antibody against human follicle stimulating hormone and the antibody against human oestradiol are mouse antibodies.

6. The method of claim 1, comprising incubating the blood sample from the equine with the antibody against human follicle stimulating hormone and the antibody against human oestradiol for about one hour in the assay, which includes addition of a luminescence signal reagent and an enhancer, and the assay result is obtained within two minutes after addition of the luminescence signal reagent and the enhancer.

* * * * *